United States Patent [19]

Svatek et al.

[11] 4,364,871

[45] Dec. 21, 1982

[54] PROCESS FOR MAKING AMINOPOLYCARBOXYLIC ACID CHELATES OF IRON

[75] Inventors: Katherine H. Svatek, Lake Jackson; David A. Wilson, Richwood; Freddie Griffin, Jr., Missouri City, all of Tex.

[73] Assignee: The Dow Chemical Company, Midland, Mich.

[21] Appl. No.: 184,848

[22] Filed: Sep. 8, 1980

[51] Int. Cl.$^3$ .............................................. C07F 15/02
[52] U.S. Cl. ................................................. 260/439 R
[58] Field of Search ................................... 260/439 R

[56] References Cited

U.S. PATENT DOCUMENTS

| | | | |
|---|---|---|---|
| 3,050,539 | 8/1962 | LeBlanc | 260/439 R |
| 3,115,511 | 12/1963 | Singer | 260/439 R |
| 3,758,540 | 9/1973 | Martell | 260/439 R |
| 3,767,689 | 10/1973 | Donovan | 260/439 R |
| 3,867,419 | 2/1975 | Iwano et al. | 260/439 R |

*Primary Examiner*—Charles F. Warren
*Assistant Examiner*—Raymond Covington
*Attorney, Agent, or Firm*—A. C. Ancona

[57] ABSTRACT

A process for making Fe-EDTA chelate comprising adding iron oxide at a ratio of <1 mole iron/mole EDTA to a mixture of $NH_4OH$ and EDTA wherein $NH_3$/EDTA mole ratio is from 1 to not more than 1.5, heating until reaction is complete, cooling to about 60° C. and adding sufficient $NH_3$ to dissolve and maintain Fe-EDTA chelate in solution, cooling to room temperature and oxidizing Fe++ to Fe+++. The process provides (1) a minimum of foaming and sludge formation during the reaction, (2) rapid dissolution of iron oxide and (3) a chelate product substantially completely in the ferric state.

3 Claims, No Drawings

PROCESS FOR MAKING AMINOPOLYCARBOXYLIC ACID CHELATES OF IRON

BACKGROUND OF THE INVENTION

Iron chelates of aminopolycarboxylic acids, e.g. ethylenediaminetetraacetic acid, are useful in numerous applications. Their aqueous solutions are employed in photographic processes, as described in U.S. Pat. No. 3,293,036, and for application to iron-deficient soils to provide that element to plants grown therein. Other uses include the removal of $H_2S$ from gas streams and as a catalyst in aqueous system processes.

In U.S. Pat. No. 3,767,689 a method for preparing aqueous solutions of iron chelates of aminopolycarboxylic acids is described. The method involves heating iron oxide and the aminopolycarboxylic acid in an aqueous medium and subsequently neutralizing with a base. The parameters employed in that process are: heating to a temperature of from 80° C. to 120° C.; a reaction period of five to 20 minutes or up to several hours with more difficulty soluble forms of iron oxide; employing about 10% excess of the aminopolycarboxylic acid over that stoichiometrically required to react with the iron oxide; and employing a ratio of 0.1 to 1 mole $NH_4OH$ per mole of aminopolycarboxylic acid (preferably 0.8 mole to form the iron-ammonium chelate and then about 1.5 moles additional to bring pH to 7 and insure neutralization of $Fe^{+++}$ chelate).

In the above patented method several problems are encountered: (1) excessive foaming and sludge formation is observed during the initial reaction of the aminopolycarboxylic acid with the iron oxide and ammonium hydroxide upon heating; (2) the end product contains about 20% of the iron in the ferrous ($Fe^{++}$) form; (3) the attempted oxidation of the ferrous iron to ferric by bubbling air through the reaction mixture during the reaction at elevated temperatures apparently decomposes the aminopolycarboxylic acid, thus reducing the amount of total chelant (the multidentate ligand molecule of the chelating agent) available to form the iron-ammonium chelate.

SUMMARY OF THE INVENTION

The present invention is a process for the preparation of an iron-aminopolycarboxylic acid chelate, totally in the ferric state. The procedure results in minimal foaming during the reaction, rapid dissolution of the iron oxide, and the absence of any sludge formation.

Foaming and sludge formation are substantially reduced by employing a mole ratio of $NH_3$/aminopolycarboxylic acid of from about 1 to 1.5 during the initial dissolution of the iron oxide. When the iron oxide is completely reacted with the chelant, the mixture is cooled and sufficient ammonia introduced to dissolve and maintain the iron chelate in solution. Finally, the reaction mixture is cooled to room temperature and contacted with oxygen (air) to convert any remaining ferrous iron to ferric.

DETAILED DESCRIPTION OF THE INVENTION

The following description shows examples to illustrate the invention and comparative examples to illustrate the art.

EXAMPLE 1

At room temperature with continuous agitation, a 10-gallon reactor was charged with 9530 milliliters distilled water and 13,474 g. (46.14 moles of ethylenediaminetetraacetic acid (EDTA). Thirty percent aqueous ammonia, 3760 ml. (59.9 moles $NH_3$) was added to the acid slurry. At this point the theoretical $NH_3$/EDTA molar ratio of 1.3 was verified by analysis. With continued stirring, 3302.5 g. iron oxide ($Fe_3O_4$) were added. This established an Fe-EDTA balance in excess of stoichiometric amounts (3% excess EDTA, by weight, based on the total weight of the system). The reactor contents were heated at 100° C. for 90 minutes with minimal foaming (<5% volume increase), rapid iron oxide dissolution, and no sludge formation. The reaction product was cooled to about 60° C. and additional aqueous ammonia was added to adjust the pH to 8.0. A clear deep reddish-brown solution resulted. Analysis of the product at this point showed 7.2% by weight total iron [2.0% ferrous ion as ferrous-EDTA, the remainder (5.2%) as ferric-EDTA] and 1.8% free (non-chelated) EDTA. This value (1.8% free EDTA) based on total weight of the system, when normalized to initial concentrations prior to the second ammonia addition, equates to 2.0%. A decrease in the amount of free EDTA present in the reaction mixture (from 3% initially to 2%) resulted from degradation of the EDTA during the heat cycle. The reaction mixture was purged with air at room temperature to oxidize the ferrous ion. Typical ferrous ion oxidation rate data is given in Table I. The resulting iron chelate solution was diluted with distilled water to 7% by weight total iron. Analysis showed it contained less than 0.07% ferrous iron.

TABLE I

| Ferrous Ion Oxidation Data | |
| --- | --- |
| Time, Hr. | % Ferrous Ion |
| 0 | 2.00 |
| 1.00 | 1.62 |
| 2.00 | 1.57 |
| 3.25 | 1.10 |
| 4.00 | 0.80 |
| 4.75 | 0.45 |
| 7.83 | 0.07 |

The rate of EDTA degradation can be reduced by use of a purge to remove dissolved oxygen from the reaction system. The following example shows preparation of iron-EDTA chelate as described in Example 1 except that a nitrogen purge was employed.

EXAMPLE 2 ($N_2$ purge)

To 511 g. distilled water at room temperature was added 755.5 g. (2.59 moles) EDTA. This mixture was ammoniated with 200 milliliters (3.18 moles) of 30% by weight aqueous ammonia. With continuous stirring, 196.7 g. of iron oxide ($Fe_3O_4$) were added. The mixture was heated at 103.5° C. for 90 minutes. The reaction mixture was purged with nitrogen during the heat cycle. Foaming was minimal, accounting for <5% volume increase. Samples were taken periodically and analyzed to determine iron-EDTA molar balance. The reaction mixture was cooled to about 60° C. and ammoniated to pH 8. Air was purged through the mixture at room temperature to oxidize ferrous ion (2.4% by analysis). Upon oxidation of the ferrous ion, the mixture was diluted with distilled water to a 7% iron product.

Another preparation, run concurrently, was made according to the method of Example 1, using the same amounts of reactants, temperatures and times employed in Example 2, but without the nitrogen purge.

EXAMPLE 3 (absence of N$_2$ purge)

To a mixture of 756 g. (2.59 moles) of ethylenediaminetetraacetic acid and 511 g. distilled water at room temperature there was added 200 milliliters (3.18 moles) of 30% aqueous ammonia. With continuous agitation, 200 g. of iron oxide (Fe$_3$O$_4$) were added. The mixture was heated at 103.5° C. for 90 minutes. Foaming produced less than 5% volume increase. Samples were taken periodically and analyzed for Fe-EDTA molar balance to monitor degradation of the EDTA. The reaction mixture as cooled to about 60° C. and ammoniated to pH 8. Air was purged through the reaction mixture at room temperature to oxidize the ferrous ion. The resulting oxidized mixture was diluted with distilled water to a 7% iron product.

Table II shows the relative rates of degradation determined for Examples 2 and 3.

TABLE II

| | Wt. % Free EDTA (based on total system weight) | |
|---|---|---|
| Time, Min. | Ex. 2 (N$_2$ purge) | Ex.3 |
| 10 | 2.5 | 2.7 |
| 15 | 2.4 | 1.4 |
| 30 | 1.0 | 0.3 excess Fe |
| 45 | 0.8 | 0.4 excess Fe |
| 65 | 0.5 | 0.3 excess Fe |

While examples are employed using iron oxide (Fe$_3$O$_4$) and EDTA as illustrative of the invention, other aminopolycarboxylic acids can be employed as the chelant moiety. Thus, representative acids are nitrilotriacetic acid, diethylenetriaminepentaacetic acid, N-hydroxyethylethylenediaminetriacetic acid, ethylenediaminetetrapropionic acid, nitrilotripropionic acid, N-hydroxyethyliminodiacetic acid, and triethylenetetraminehexaacetic acid.

The following examples were in accordance with the teachings of U.S. Pat. No. 3,767,689.

COMPARATIVE EXAMPLE A

Ethylenediaminetetraacetic acid (754 g., 2.58 moles) was added to 512 g. distilled water. One hundred thirty milliliters (2.06 moles) of 30% aqueous ammonia were added to the acid slurry to achieve an ammonia/EDTA molar ratio of 0.8. With continuous agitation, 198.4 g. of iron oxide (Fe$_3$O$_4$) were added. The reaction mixture was heated to 100° C. at which point it began to foam exceedingly resulting in an 80% increase in volume. The foaming was followed by heavy sludge formation which was difficult to stir. Any sampling of the system at this point would have been futile due to solid formation and non-homogeneity of the mixture.

Following the reaction (45 minute heat cycle), additional 30% aqueous ammonia was added, after cooling to about 60° C., to neutralize the product and raise the pH of the solution to 7.5. The mixture was diluted to form a 7% iron product. Analysis of the final product showed 1.5% ferrous iron (or ~20% of the total iron was in the ferrous state).

In an attempt to prepare a totally ferric-EDTA chelate, a run was made utilizing an air purge during the heat cycle to oxidize ferrous ion. See below.

COMPARATIVE EXAMPLE B

To a mixture of 512 g. distilled water and 758 g. (2.60 moles) EDTA at room temperature, 200 ml. (3.18 moles NH$_3$) of 30% aqueous ammonia were added. With continuous stirring, 194 g. of iron oxide (Fe$_3$O$_4$) were added.

The reactor contents were heated at 100.5° C. for 90 minutes with an air purge. Following the heat cycle, the product was cooled to about 60° C., then ammoniated to pH 8.0 and diluted with distilled water. The final product contained 7% total iron (1.5% ferrous ion, 5.5% ferric ion).

Other oxides of iron, e.g. FeO and Fe$_2$O$_3$, are also useful in preparing the ferric chelate, recognizing that the ferrous ion must be completely converted to the ferric when using FeO, which would perhaps lengthen the total process.

Temperatures operable in the present invention are within the range of 85° to 105° C. with a preferred range being from about 95° to 100° C.

Lower temperatures result in slow and/or incomplete iron oxide dissolution; higher temperatures increase the rate of aminopolycarboxylic acid degradation, both of which results are undesirable.

Reaction times are determined by the time required to completely dissolve the iron oxide. Reaction times as short as 15 minutes have been utilized resulting in small amounts of unreacted iron oxide. Heating times in excess of that required for complete iron oxide dissolution allow for aminopolycarboxylic acid degradation.

The initial mole ratios of NH$_3$ to chelant, e.g. EDTA, are from 1.0 to 1.5 with the preferred range being 1.2-1.3. Molar ratios less than 1.0 result in extensive foaming and sludging while values greater than 1.5 result in very slow and/or incomplete iron oxide dissolution.

In the process of the present invention, it is necessary to use an excess of chelant based on a stoichiometric 1:1 molar ratio of iron to chelant. The iron may be present in an amount within the range of from about 0.8 to about 0.96 mole per mole of chelant, but is preferably about 0.90-0.94. In terms of weight percent of the total system 2-9% excess may be employed, but a preferred excess of chelant is from about 2-4%. Free EDTA in excess of 4% may be used but is not economically attractive. Smaller amounts of free EDTA (i.e., less than 2%) can be utilized provided some excess EDTA remains following the reaction for product stability.

The ammonia is normally provided as concentrated NH$_4$OH (about 30% NH$_3$), but anhydrous ammonia can be employed.

Thus, the improved process of the present invention provides (1) minimal foaming and no sludge, (2) a product in which substantially all the iron is in the ferric state and (3) a reduction in the rate of decomposition of the chelant during the reaction.

The steps of the process of forming the iron chelate which it is desired to patent are: (1) providing a mixture (slurry) of NH$_4$OH and aminopolycarboxylic acid chelant in an aqueous system wherein (2) the NH$_3$/chelant ratio is at least 1.0 but no more than 1.5, (3) heating said mixture to a temperature of from about 85° to about 105° C. while (4) introducing less than a stoichiometric amount of iron oxide to form an iron-ammonium-chelant product, (5) heating said mixture until the reaction is complete, optionally in the substantial absence of oxygen, (6) cooling to a temperature of from about 45°–75° C. and adding sufficient ammonia to dissolve and to maintain the iron chelate in solution, and (7) cooling said reaction mixture to room temperature and contacting with an oxidizing agent for a sufficient time to ensure that the iron is substantially all in the ferric state.

We claim:

1. An improved process for producing a ferric-ammonium-chelate of ethylenediaminetetraacetic acid (EDTA) wherein an oxide of iron is reacted with said EDTA in the presence of a base, which comprises: (1) providing a mixture in water of ammonia together with said EDTA in a molar ratio of ammonia to EDTA of at least 1.0 but not more than 1.5, (2) adding to said mixture said oxide of iron at less than 1 mole of iron per mole of EDTA, (3) heating said mixture to a reaction temperature within the range of from about 85° to about 105° C., and conducting said reaction in the substantial absence of oxygen, (4) maintaining said reaction temperature for a time sufficient to complete the reaction, (5) cooling said mixture to a temperature within the range of from about 45° to 80° C., (6) introducing ammonia to said mixture in sufficient amount to dissolve and to maintain in solution the iron chelate so formed, (7) cooling said chelate solution to room temperature and (8) oxidizing any ferrous ion present in said chelate solution to the ferric ion.

2. The process of claim 1 wherein the reaction mixture is made substantially oxygen-free by purging said mixture with an inert gas and employing said inert gas as a pad.

3. The process of claim 2 wherein the inert gas is nitrogen.

* * * * *